(12) United States Patent
Kallmann

(10) Patent No.: US 7,999,948 B2
(45) Date of Patent: Aug. 16, 2011

(54) INTERFEROMETRIC SYSTEM FOR THE USE OF SPECIAL-PURPOSE OPTICAL SYSTEMS

(75) Inventor: Ulrich Kallmann, Tuebingen (DE)

(73) Assignee: Robert Bosch GmbH, Stuttgart (DE)

( * ) Notice: Subject to any disclaimer, the term of this patent is extended or adjusted under 35 U.S.C. 154(b) by 507 days.

(21) Appl. No.: 11/547,953

(22) PCT Filed: Feb. 28, 2005

(86) PCT No.: PCT/EP2005/050838
§ 371 (c)(1),
(2), (4) Date: Aug. 21, 2008

(87) PCT Pub. No.: WO2005/098398
PCT Pub. Date: Oct. 20, 2005

(65) Prior Publication Data
US 2008/0304071 A1 Dec. 11, 2008

(30) Foreign Application Priority Data
Apr. 5, 2004 (DE) .................. 10 2004 017 229

(51) Int. Cl.
*G01B 11/02* (2006.01)
(52) U.S. Cl. ........................................... 356/511
(58) Field of Classification Search .................. 356/497, 356/511–514
See application file for complete search history.

(56) References Cited

U.S. PATENT DOCUMENTS

| | | | | |
|---|---|---|---|---|
| 5,390,023 A | * | 2/1995 | Biegen | .......................... 356/497 |
| 5,975,697 A | | 11/1999 | Podoleanu et al. | |
| 6,191,862 B1 | | 2/2001 | Swanson et al. | |
| 2003/0011784 A1 | | 1/2003 | De Groot et al. | |
| 2003/0048532 A1 | * | 3/2003 | Lindner et al. | ................. 359/511 |
| 2004/0059540 A1 | * | 3/2004 | Matsumoto et al. | .......... 702/150 |
| 2006/0238774 A1 | * | 10/2006 | Lindner et al. | ................. 356/511 |

FOREIGN PATENT DOCUMENTS

| | | |
|---|---|---|
| DE | 43 09 056 | 9/1994 |
| DE | 100 47 495 | 10/2001 |
| DE | 101 15 524 | 11/2001 |
| DE | 101 62 180 | 7/2003 |
| JP | 2008520053 | 9/2003 |
| JP | 2008529753 | 10/2003 |
| WO | 92 19930 | 11/1992 |
| WO | WO 01/27558 | 4/2001 |
| WO | WO 01/75395 | 10/2001 |

OTHER PUBLICATIONS

M.W. Lindner "White Light Interferometry Via an Endoscope", Jul. 8-10, 2002, Proc SPIE, vol. 4777, pp. 90-101.

* cited by examiner

*Primary Examiner* — Michael A Lyons
(74) *Attorney, Agent, or Firm* — Kenyon & Kenyon LLP

(57) ABSTRACT

An interferometric system which includes an illumination arm having a light source and an illumination optical system for forming an illumination beam path; an object arm having a special-purpose optical system for measuring an object for the purpose of forming an imaging beam path; a reference arm having an adjusting element and a reference element coupled thereto; a detector arm having a detector; and a beam splitter, an at least partially transparent dispersion-compensating medium being provided in the reference arm for compensating the dispersion of the optical components of the object arm, the dispersion-compensating medium being exchangeable and also being adjusted to the special-purpose optical system. This enables a universal white light interferometer platform to be provided for enabling different measuring tasks to be carried out simply by exchanging the special-purpose optical systems.

12 Claims, 3 Drawing Sheets

INTERFEROMETRIC SYSTEM FOR THE USE OF SPECIAL-PURPOSE OPTICAL SYSTEMS

FIELD OF THE INVENTION

The present invention relates to an interferometric system which includes an illumination arm having a light source and an illumination optical system for forming an illumination beam path; an object arm having a special-purpose optical system for measuring an object for the purpose of forming an imaging beam path; a reference arm having an adjusting element and a reference element coupled thereto; a detector arm having a detector; and a beam splitter, an at least partially transparent dispersion-compensating medium being provided in the reference arm for compensating the dispersion of the optical components of the object arm.

BACKGROUND INFORMATION

The manufacture of precision parts requires measurement methods for detecting the geometry and condition of the parts to ensure the quality of such parts. Optical measurement methods, for example imaging and image evaluation, interferometry, and white light interferometry play an important role in this process.

The principle of the white light interferometer is based on the fact that a short-coherent light source is used for illuminating an imaging system. In addition to the normal imaging optical system, the imaging system also has a reference arm through which a portion of the incident light passes. If the propagation path of light $\Lambda_O$ in the object arm differs from the propagation path in reference arm $\Lambda_R$ by an amount which is less than coherence length $l_c$ of the light, i.e., $$|\Lambda_R - \Lambda_O| < l_c \quad (1)$$

the recombined light fields may have a measurable interference. This is utilized by varying the path difference of the light fields in a defined manner during the measurement and simultaneously measuring the intensity of the recombined light fields on a planarly measuring detector, usually a CCD camera. The pixel-by-pixel evaluation of the intensity modulation generated by the interference, the intensity correlogram, supplies unambiguous height information for each individual pixel. When carried out for the entire pixel field, this results in complete height information for the object.

Commercial white light interferometers typically have the following specifications:

Height resolution $\Delta z$ is specified by the average wavelength of light $\mu_m$, coherence length $l_c$ and the type of correlogram evaluation algorithm used. Typical parameters such as $\lambda_m = 600$ nm, $l_c = 2$ μm provide values of $\Delta z = 1$ nm.

Lateral resolution $\delta$ resembles that of a conventional imaging system and, in principle, is limited by $\lambda_m$ and numerical aperture NA of the imaging optical system.

$$\delta \geq 0.61 \zeta_m / NA \quad (2)$$

Maximum measurable total height difference $z_{max}$ is determined from the technical feasibility of producing a path difference in the reference arm and object arm which is precisely guided over the entire distance. Regulated piezoelectric systems currently support values of $z_{max} \leq 400$ μm.

Conventional interferometers, in particular white light interferometer systems, may be used for the tasks described above if the location to be measured is easily accessible and has a largely flat geometry. If this is not the case, interferometers are used which have a special-purpose optical system which is adjusted to the object to be measured.

For example, interferometers having endoscopic optical systems are known (Lindner MW 2002 "White Light Interferometry Via an Endoscope" Proc SPIE 4777: 90-101) which enable hard-to-reach locations to be measured. The optical endoscope is characterized by the fact that the imaging lenses may be placed so close to the object that numerical aperture NA in equation (2) assumes values which support an adequate resolution $\delta$.

German Published Patent Application No. 101 15 524 describes a white light interferometer in which an optical system for generating a flat intermediate image is situated in the measuring light path. However, the object in this case is to provide a depth scan.

German Published Patent Application No. 100 47 495 describes a white light interferometer having an intermediate image which uses an endoscope for measurements in deep, narrow holes and has a depth resolution of several nanometers.

A measurement system in which the reference arm accommodates an electrically controllable filter for adjusting the intensities of the reference and measuring beams is known from German Published Patent Application No. 101 62 180.

Panoramic optical systems are an important type of special-purpose optical system for white light interferometers, which are adjusted to the component. They provide images of objects positioned at a large angle relative to the optical axis.

However, these optical systems have the disadvantage that the architecture of the interferometric system is determined by the special-purpose optical system to the extent that the system may not be used for any other measuring task using a different special-purpose optical system.

SUMMARY OF THE INVENTION

The object of the present invention is to provide an interferometric system in which the system has a flexible design and may be adjusted to the measuring tasks with a minimum of effort.

The object of the present invention is achieved by the fact that the dispersion-compensating medium is exchangeable and is also adjusted to the special-purpose optical system. This enables different special-purpose optical systems to be used, while minimizing modifications of the interferometer. The interferometer may therefore be used universally and is adjustable to a wide range of measuring tasks, including those which are as yet unknown at the time of its design.

If the length of the reference arm is adjusted to the length of the object arm, special-purpose optical systems of varying optical length may be used.

In a preferred embodiment, the dispersion-compensating medium is made of glass. Due to the many different variants of optical glass, the medium may be adjusted to a wide range of special-purpose optical systems. Glass bodies of this type are also easily exchangeable.

If an intermediate image is produced in the object arm, an unambiguous interface may be defined for exchangeable special-purpose optical systems.

According to an embodiment which is designed for industrial use, a telecentric imaging beam path is formed in the object arm and in the detector arm leading to the detector. This largely prevents magnification errors, image errors, and angle errors, which favors the use of different special-purpose optical systems.

The telecentric beam path in the object arm is duplicated particularly well in the reference arm by situating at least one lens in the reference arm.

An easy adjustability to different measuring tasks is achieved by providing a mechanical device for changing the special-purpose optical system in the object arm.

If the illumination beam path is essentially parallel at the location of the intermediate image, the object may be illuminated by parallel light. This achieves a particularly good imaging quality.

Designing the diameter of the parallel illumination beam path to have variable settings enables the illuminated, and thus measured, surface to be selected.

A particularly good adjustment to different optical characteristics of the special-purpose optical systems as well as to the object surface is achieved by enabling the illuminance and/or the spectral characteristic of the illuminating light to have variable settings.

A particularly easy adjustment of the illuminance is achieved by positioning a preferably variable diaphragm in the illumination arm.

If a filter is situated in the illumination arm, the spectral characteristic of the illumination light may be particularly easily adjusted to the measuring task.

An advantageous embodiment for a simple, universal design is provided by the fact that a special-purpose optical system adjusted to the object is designed in such a way that the optical path lengths of the beams reflected back from different object points are compensated by the special-purpose optical system with regard to the reference surface defined by the wave front of the reference arm.

BRIEF DESCRIPTION OF THE DRAWINGS

FIG. 3a shows a schematic representation of an exemplary embodiment for a measuring task.

FIG. 3b shows a schematic representation of the beam path for the measuring task according to FIG. 3a.

DETAILED DESCRIPTION

Figure 1:
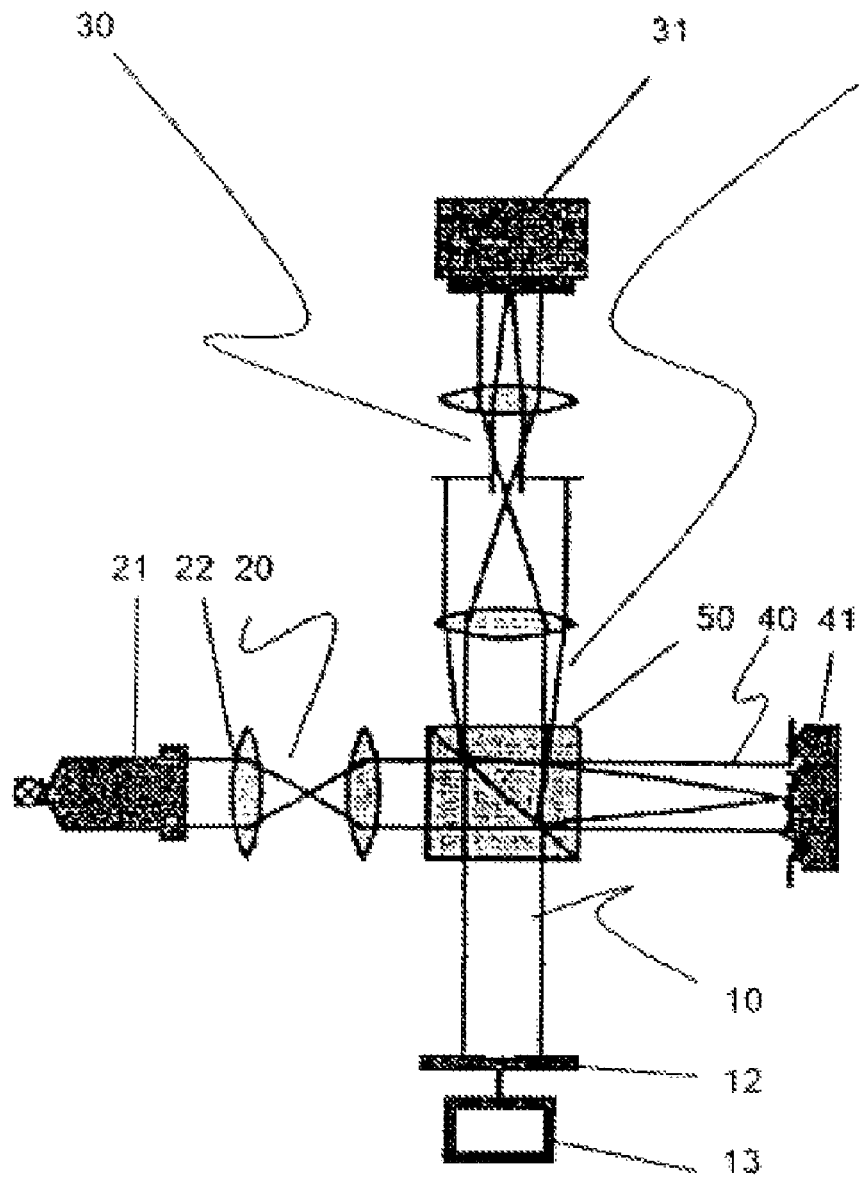
FIG. 1 shows a schematic representation of a white light interferometer system according to the related art.

Interferometric system 1 of the white light interferometer system according to the related art, which is illustrated schematically in FIG. 1, includes an object arm 40 in which the surface to be measured of an object 41 is positioned, and an illumination arm 20 which has a light source 21 and an illumination optical system 22 including one or more lenses. Interferometric system 1 has a reference arm 10, including a reference element 12, which is positioned orthogonally in relation to illumination arm 20 and object arm 40 and is mechanically coupled to an adjusting element 13, usually a piezoelectric system. A detector arm 30 which includes a detector 31, usually a planarly measuring detector 31 such as a CCD camera, is positioned diametrically opposed to reference arm 10. An evaluation device (not illustrated in greater detail) is provided for evaluation purposes.

A beam splitter 50 splits and recombines the different light beams so that the light beams from reference arm 10 and those from object arm 40 may interfere in the manner described above at detector 31 in detector arm 30. The architecture of an interferometric system 1 according to the related art is thus largely defined. Changes to the design which may result from different measuring tasks are possible only to a limited extent.

Figure 2:
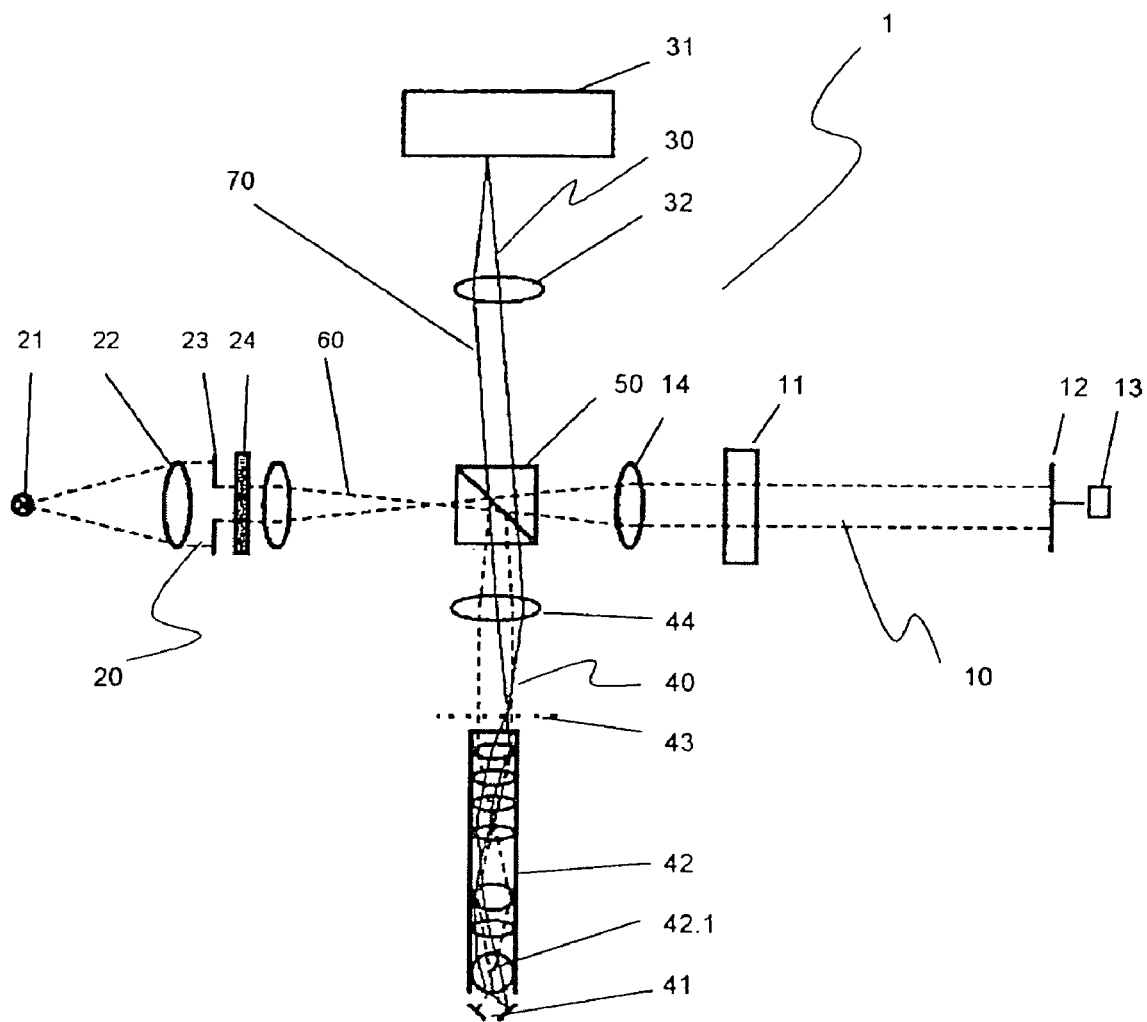
FIG. 2 shows a schematic representation of an interferometric system in an embodiment according to the present invention.

In contrast, FIG. 2 shows an interferometric system 1 in which, according to the present invention, different measuring tasks may be performed by a simple adjustment of the interferometer architecture.

Interferometric system 1 includes an illumination arm 20 having a light source 21 and an illumination optical system 22, and an object arm 40 having a special-purpose optical system 42 for measuring, for example, hard-to-reach surfaces of an object 41. In the illustrated exemplary embodiment, the special-purpose optical system is designed as an endoscope and, using for example a panoramic optical system 42.1 having a spherical lens at the end of the endoscope, enables the imaging of objects 41 which are positioned at a large angle relative to the optical axis.

An adjusting element 13, usually a piezoelectric system, and a reference element 12 mechanically coupled thereto and designed as a flat reference mirror, are situated in reference arm 10, enabling a depth scanning of object 41. Detector arm 30 includes a detector 31 designed as a CCD camera which may be used to carry out an extensive, pixel-by-pixel evaluation of the intensity modulation generated by the interference, the detector supplying unambiguous height information for each individual pixel and thus for the surface of object 41. Another way to perform the depth scan is to move interferometric system 1, with or without special-purpose optical system 42, relative to object 41.

An illumination beam path 60 is supplied from light source 21, via illumination optical system 22 to beam splitter 50, which allows a portion of the light to pass into reference arm 10. A portion of the light is diverted to illuminate object 41 into object arm 40. The light reflected by the object is supplied to detector arm 30 in the form of illumination beam path 70. In detector arm 30, illumination beam path 70 (reflected reference beam) may interfere with illumination beam path 60 reflected back by reference mirror 12.

According to the present invention, a dispersion-compensating medium 11, which compensates the dispersion of special-purpose optical system 42 and is at least partially transparent, is introduced into reference arm 10. In a preferred embodiment, dispersion-compensating medium 11 is exchangeable and may be adjusted to the optical characteristics of special-purpose optical system 42. It is also conceivable to adjust the length of reference arm 10 to special-purpose optical system 42.

In a preferred specific embodiment, dispersion-compensating medium 11 is made of at least one glass body which, in combination with the other components of reference arm 10, has approximately the same dispersion as the components of object arm 40. In other embodiments, at least partially transparent plastic bodies or vessels filled with fluid or gas are also conceivable.

This system enables different special-purpose optical systems 42 to be used in a single interferometric system 1. The necessary adjustment of the dispersion in reference arm 10 is easily achieved by exchanging dispersion-compensating medium 11 and, if necessary, adjusting the length of reference arm 10.

The exemplary embodiment illustrated in FIG. 2 also includes a lens system in object arm 40 which has a lens 44 which may be used to generate an intermediate image 43 in the region between lens 44 and special-purpose optical system 42, the intermediate image being mapped to detector 31 by a telecentric imaging beam path 70 in object arm 40 and detector arm 30. Telecentric optical systems designed in this manner are intended, in particular, for the use of industrial image processing systems and largely prevent magnification errors, image errors, and angle errors. Different working distances from the object do not affect the scaling of the image, which enables, in particular, different special-purpose optical systems 42 to be exchanged. Illumination beam path 60 is ideally designed in such a way that a parallel beam path is formed at the location of intermediate image 43.

According to a preferred embodiment, a mechanical device for changing special-purpose optical system 42 is preferably provided between telecentric imaging beam path 70 and special-purpose optical system 42 so that special-purpose optical system 42 is easily exchangeable in a manner similar to a reflex camera. Quarter-turn or threaded fasteners are advantageous in this case.

Illumination optical system 22 in illumination arm 20 may have a variable diaphragm 23 which may be used to vary the illumination aperture in such a way that the diameter of parallel illumination beam path 60 may be variably set at the location of intermediate image 43. In addition to a variable setting of the illuminance, a filter 24 may be situated in illumination arm 20 in equally preferred embodiments, enabling the spectral characteristic and thus the resolution conditions to be modified. Filter systems which enable variable settings are particularly preferred. Furthermore, it is advantageous if the illuminance is also infinitely variable, for example using a neutral wedge filter.

According to one exemplary embodiment, an interferometric system 1 having the features described above is used for inspecting internal combustion engines, in particular for the quality control of valve seats in diesel injection systems.

Figures 3A, 3B:
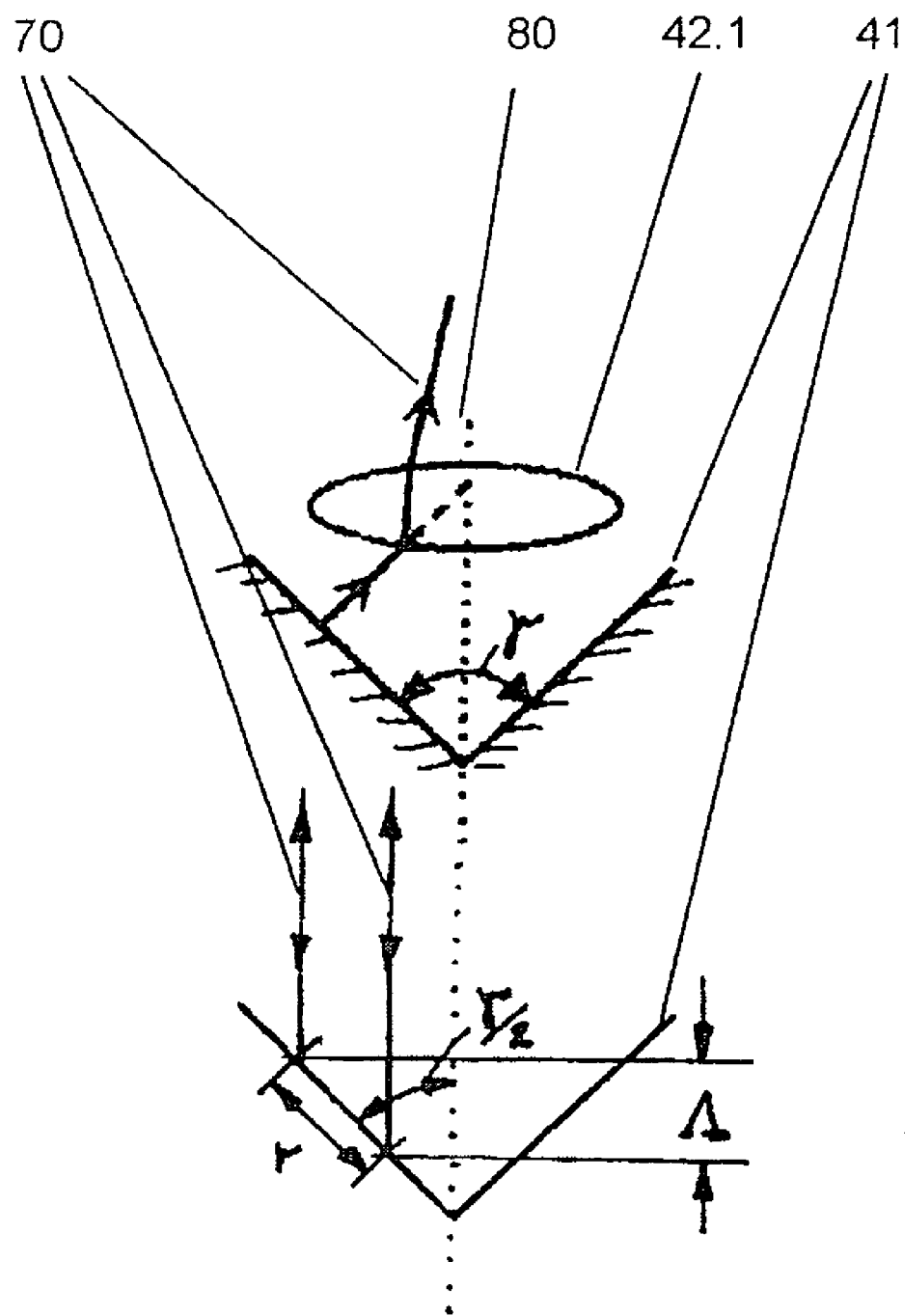

FIG. 3a shows a schematic representation of a measuring task of this type. In this case, special-purpose optical system 42 has a panoramic optical system 42.1. This system provides images of objects positioned at a large angle relative to an optical axis 80. Panoramic optical systems of this type are used, for example, to measure valve seats, for example by detecting cone angle γ, the roundness along the sealing edge and surface characteristics such as roughness.

Geometrically, the shape of valve seats largely corresponds to that of female taper surfaces. FIG. 3b shows a schematic representation of the geometry. Assuming ideal surfaces, imaging the female taper results in an intensity curve of the generated interference bands of $$I_{(r)} = \text{const}.I_o\{1 - I_m \cos((2\pi/\lambda_m)2\cos((\gamma/2)r)\} \quad (3)$$

where r is the radial direction on the conical surface, $I_o$ the average intensity and $I_m$ the intensity modulation generated by the interference. The condition for adjacent interference maxima is $$\Lambda = \lambda/2 = r\cos(\gamma/2) \quad (4)$$

Equation (3) demonstrates that the intensity is modulated by a period length Π of $$\Pi = \lambda_m/(2\cos(\gamma/2)) \quad (5)$$

The ability to see the interference bands requires a resolution which is better than period length Π.

It is possible to increase period length Π by using reference elements 12 adjusted to the shape of the object. This reduces the requirement to be met by the optical resolution of the system. However, reference element 12 (in addition to dispersion compensation elements 11) must be adjusted to object 41 to be measured, which requires a certain amount of effort.

Using a special-purpose optical system 42 adjusted to object 41, it is possible to further increase period length Π in such a way that the optical path lengths of different object points are compensated by a special-purpose optical system 42 with regard to the (virtual) reference surface defined by the wave front of reference arm 10.

For example, if the reference surface is flat, special-purpose optical system 42 is designed so that object 41 is mapped at least approximately to a corresponding plane.

In this embodiment of interferometric system 1, a high resolution of the image and detection device is no longer decisive, in particular, for example, if the roundness or cone angle of object 41 is to be measured.

This interferometric system 1 enables sharp images to be produced, no relative movement between special-purpose optical system 42 and object 41 being needed during the measurement for refocusing. As a result, endoscope geometries such as curved or very long endoscopes may also be used. The depth scan is carried out by the movement of a reference element 12 in reference arm 10.

Reference arm 10 is part of an interferometric platform. The modification of the imaging optical system requires a one-time modification of the optical length of reference arm 10 and the adjustment of dispersion-compensating medium 11, which is easily accomplished by its exchangeability.

In summary, an interferometric system 1 according to the present invention may be used to provide a universal white light interferometer platform which enables different measuring tasks to be carried out by simply exchanging special-purpose optical systems 42. This also enables even interferometric measurement systems which are resistant to environmental influences to be produced.

What is claimed is:

1. An interferometric system, comprising:
   a light source;
   an illumination arm including an illumination optical system for forming an illumination beam path;
   an object arm including a lens system having a lens, and a special-purpose optical system for measuring an object for the purpose of forming an imaging beam path, wherein the lens generates an intermediate image in the object arm next to the special-purpose optical system in the region between the lens and the special-purpose optical system;
   a reference arm including an adjusting element and a reference element coupled thereto;
   a detector arm including a detector; and
   a beam splitter, wherein:
   an at least partially transparent dispersion-compensating medium is provided in the reference arm to compensate a dispersion of optical components of the object arm, and
   the dispersion-compensating medium is exchangeable and is also adjusted to the special-purpose optical system.

2. The device as recited in claim 1, wherein a length of the reference arm is adjusted to a length of the object arm.

3. The device as recited in claim 1, wherein the dispersion-compensating medium is made of glass.

4. The device as recited in claim 1, wherein a telecentric imaging beam path is formed in the object arm and the detector arm leading to the detector.

5. The device as recited in claim 1, further comprising:
   at least one lens situated in the reference arm.

6. The device as recited in claim 1, further comprising:
   a mechanical device for changing the special-purpose optical system provided in the object arm.

7. The device as recited in claim 1, wherein the illumination beam path at a location of the intermediate image is formed to be essentially parallel.

8. The device as recited in claim 7, wherein a diameter of the parallel illumination beam path is variably settable.

9. The device as recited in claim 1, wherein at least one of an illuminance and a spectral characteristic of an illumination light is variably settable.

10. The device as recited in claim 1, further comprising:
a preferably variable diaphragm situated in the illumination arm.

11. The device as recited in claim 1, further comprising:
a filter situated in the illumination arm.

12. The device as recited in claim 1, wherein: the special-purpose optical system adjusted to the object is designed in such a way that optical path lengths of beams reflected back from different object points are compensated by the special-purpose optical system with regard to a reference surface defined by a wave front of the reference arm.

* * * * *